(12) United States Patent
Ling et al.

(10) Patent No.: US 11,164,311 B2
(45) Date of Patent: Nov. 2, 2021

(54) IMAGING APPARATUS, IMAGE DISPLAY SYSTEM, AND IMAGE DISPLAY METHOD

(71) Applicant: FUJIFILM Corporation, Tokyo (JP)

(72) Inventors: Xiao Ling, Ashigara-kami-gun (JP); Junichi Mori, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 126 days.

(21) Appl. No.: 16/568,442

(22) Filed: Sep. 12, 2019

(65) Prior Publication Data
US 2020/0005457 A1    Jan. 2, 2020

Related U.S. Application Data

(63) Continuation of application No. PCT/JP2017/041046, filed on Nov. 15, 2017.

(30) Foreign Application Priority Data

Mar. 16, 2017 (JP) .............................. JP2017-051264

(51) Int. Cl.
*G06T 7/00* (2017.01)
*A61B 5/00* (2006.01)
*A61B 5/103* (2006.01)

(52) U.S. Cl.
CPC .......... *G06T 7/0012* (2013.01); *A61B 5/0059* (2013.01); *A61B 5/1032* (2013.01);
(Continued)

(58) Field of Classification Search
CPC ....... A61B 5/441; A61B 5/489; A61B 5/0053; A61B 5/1032; A61B 5/0059;
(Continued)

(56) References Cited

U.S. PATENT DOCUMENTS

| 5,146,923 A | 9/1992 | Dhawan |
|---|---|---|
| 2013/0148326 A1 | 6/2013 | Goldfain |

(Continued)

FOREIGN PATENT DOCUMENTS

| JP | 60-060832 A | 4/1985 |
|---|---|---|
| JP | 2006-051279 A | 2/2006 |

(Continued)

OTHER PUBLICATIONS

International Search Report dated Dec. 26, 2017 from the International Searching Authority in counterpart International Application No. PCT/JP2017/041046.

(Continued)

*Primary Examiner* — Brenda C Bernardi
(74) *Attorney, Agent, or Firm* — Sughrue Mion, PLLC

(57) ABSTRACT

Provided are an imaging apparatus, an image display system, and an image display method that can observe a papillary structure and a capillary in a papillary process at the same time. The imaging apparatus includes: an illumination unit that irradiates a surface of a skin with illumination light; an imaging unit that captures transmitted light reflected from the inside of the skin; a light shielding unit that is brought into close contact with the surface of the skin, is used, and is provided so as to prevent light reflected from the surface of the skin from reaching the imaging unit; and a pressing unit having a distal end that presses the surface of the skin in order to curve an epidermis of the skin to be captured.

26 Claims, 11 Drawing Sheets

(52) U.S. Cl.
 CPC .... *A61B 5/441* (2013.01); *G06T 2207/30088* (2013.01); *G06T 2207/30101* (2013.01)

(58) Field of Classification Search
 CPC ......... G06T 7/0012; G06T 2207/30088; G06T 2207/30101; G01N 21/27
 See application file for complete search history.

(56) References Cited

U.S. PATENT DOCUMENTS

| | | | |
|---|---|---|---|
| 2015/0025343 A1 | 1/2015 | Gareau et al. | |
| 2015/0223749 A1 | 8/2015 | Park et al. | |
| 2016/0310023 A1* | 10/2016 | Chachisvilis | A61B 8/06 |

FOREIGN PATENT DOCUMENTS

| | | |
|---|---|---|
| JP | 2013-236758 A | 11/2013 |
| JP | 2015-152601 A | 8/2015 |
| JP | 2015-205222 A | 11/2015 |
| JP | 2016-010641 A | 1/2016 |
| KR | 1020160061978 A | 6/2016 |
| WO | 2008010604 A1 | 1/2008 |
| WO | 2015/085240 A1 | 6/2015 |

OTHER PUBLICATIONS

Written Opinion dated Dec. 26, 2017 from the International Bureau in counterpart International Application No. PCT/JP2017/041046.
International Preliminary Report on Patentability dated Sep. 17, 2019 from the International Bureau in counterpart International Application No. PCT/JP2017/041046.
Extended European Search Report dated Jan. 17, 2020 in European Application No. 17900401.5.
Communication dated Feb. 19, 2021, from the Korean Intellectual Property Office in application No. 10-2019-7026882.

* cited by examiner

IMAGING APPARATUS, IMAGE DISPLAY SYSTEM, AND IMAGE DISPLAY METHOD

CROSS-REFERENCE TO RELATED APPLICATIONS

This application is a Continuation of PCT International Application No. PCT/JP2017/041046 filed on Nov. 15, 2017, which claims priority under 35 U.S.C. § 119(a) to Japanese Patent Application No. 2017-051264 filed on Mar. 16, 2017. The above application is hereby expressly incorporated by reference, in its entirety, into the present application.

BACKGROUND OF THE INVENTION

1. Field of the Invention

The present invention relates to an imaging apparatus, an image display system, and an image display method, and more particularly, to an imaging apparatus, an image display system, and an image display method that can non-invasively acquire an image of a papillary structure or a capillary in a papillary layer (papillary process) and display the image.

2. Description of the Related Art

The human skin tissue (skin) S has a layered structure as illustrated in the image of FIG. 14 and is divided into an epidermis 82, a dermis 84, and a subcutaneous tissue (not illustrated) in this order from the outermost layer. The epidermis 82 is a membrane including a horny layer 80 that is the outermost layer of the skin and comes into contact with the outside and a basal layer 86 that comes into contact with the dermis 84. The dermis 84 is a membrane including a papillary layer 88 that comes into contact with the basal layer 86 of the epidermis 82 and a reticular layer 90 that comes into contact with the subcutaneous tissue.

As illustrated in FIG. 15 which is a diagram schematically illustrating the skin tissue S, a bumpy papillary structure in which the epidermal processes 87 of the basal layer 86 of the epidermis 82 and the papillary processes 89 of the papillary layer 88 of the dermis are engaged with each other is formed between the epidermis 82 and the dermis 84.

The subcutaneous tissue includes the arteries and the veins that play an important role in the supply of nutrients to the skin, metabolism to carry out waste products, and thermoregulation. The arteries and the veins in the subcutaneous tissue are connected to the blood vessels (reticular layer blood vessels) 92 in the reticular layer 90 of the dermis 84 and supply nutrients and oxygen to the epidermis 82 in which the blood vessels are absent through the capillaries 94 in the papillary processes.

In the skin tissue S, it is pointed out that, in a case in which the unevenness of the papillary structure is reduced and the surface area of the papillary processes 89 is reduced due to, for example, aging, the supply of nutrients and oxygen from the capillaries 94 in the papillary processes to the epidermis 82 is delayed. As a result, the skin is not contracted and expanded and gradually sags. That is, it is considered that the papillary structure and the capillary in the papillary process are closely related to skin nourishment, metabolism, thermoregulation, and the state of the skin (for example, firmness, wrinkles, and sagging).

Therefore, in a case in which it is possible to appropriately observe the papillary structure and the capillary in the papillary process, it is possible to evaluate the state of the skin and to check a change in the skin due to aging. As a result, it is possible to examine the effects of cosmetics, skin care products, and skin care and thus to apply the configuration to the research or cosmetics and the development of products.

Methods of observing the internal structure of the skin S include an invasive observation method and a method for observing the skin in a non-invasive manner.

Many of the invasive observation methods according to the related art perform a chemical treatment for skin tissue pieces collected from the human body and observe the skin tissue pieces.

In recent years, for example, a method for acquiring an image of the inside of the skin using a confocal microscope and the following methods have been proposed as the non-invasive observation method.

JP2015-152601A discloses an apparatus in which light is emitted from a light source to the surface of the skin, is incident on the skin, and is reflected from the inside of the skin and a photodetector receives light transmitted through the skin to acquire the image of the skin.

This apparatus further includes a body obtained by connecting the light source and the photodetector. The body has an opening portion through which light can be emitted from the light source to the outside, an opening portion through which light can be received to the photodetector from the outside, and a cover that covers the light source and the photodetector except the opening portions.

JP2013-236758A discloses an apparatus in which a light source is brought into close contact with the surface of the skin and emits light, a detection unit detects light reflected from a living body, and an image (for example, an image focused on the epidermis or the dermis) of the inside of the skin is generated on the basis of the output (measurement data) from the detection unit. In addition, the following are disclosed: an apparatus in which a light source is provided around a detection unit; and a configuration in which the apparatus further comprises a light shielding wall that prevents light emitted from the light source from being incident on the detection unit.

WO2008/010604A discloses a blood vessel imaging apparatus including a hollow body that has an opening end with a shape capable of coming into close contact with the skin, an irradiation unit that is provided at the edge of the opening end or in the vicinity of the edge and emits light to the vicinity of an examination target part coming into contact with an opening portion in the hollow body, an imaging unit that receives the light emitted from the inside of the examination target part to the hollow body, and pressure reduction means for sucking a portion of the examination target part into the hollow body. In addition, a technique is disclosed which captures a blood vessel distribution of the vein using this apparatus.

SUMMARY OF THE INVENTION

The invasive observation method is suitable for accurately checking the shape or number of papillary structures. However, since the method damages the skin, collects tissue pieces, and observes the tissue pieces, it is difficult to observe a change in the papillary structure and the capillary in the papillary process at the same observation position (that is, a collection target position) over time and to investigate in detail a change in other parts associated with the change and the influence of the change.

In the method using a confocal microscope, since an operation method is extremely complicated, in practice, it is difficult to observe the human skin in a non-invasively manner using the microscope.

In addition, the diameter of the apex of a capillary loop in the papillary process is 7.5 to 10 µm and is wide enough for red blood cells to pass in one row. Since a blood flow in the capillary in the papillary process is adjusted in relation to thermoregulation, blood does not always flow through the capillary in the papillary process. That is, the number of capillaries in the papillary processes that can be observed changes greatly depending on conditions (for example, temperature, humidity, and the physical condition and constitution of the subject). Therefore, it is difficult for the apparatus disclosed in JP2015-152601A and JP2013-236758A which captures the image of the skin without adjusting a blood flow in the capillaries to observe all of the capillaries in the papillary layer. As a result, many capillaries are likely to be missed.

In the apparatus disclosed in WO2008/010604A, in a case in which the skin is sucked by the pressure reducing means, such as a pressure reducing pump, a capillary with a very small inner diameter is broken and internal bleeding occurs, which makes it difficult to accurately perform measurement. In addition, there is a problem that the cost for the pressure reducing means increases and it takes a lot of time and effort required for pressure reduction.

Further, in the images captured by the apparatuses disclosed in JP2015-152601A, JP2013-236758A, and WO2008/010604A, it is very difficult to distinguish and observe the capillary in the papillary process and the blood vessel in the reticular layer.

As described above, the observation methods according to the related art include a method for observing a skin tissue piece collected from the human body, a method for observing the skin a non-invasive manner, and a combination of the results of these methods. Therefore, in the observation method according to the related art, it is difficult to simultaneously observe both the papillary structure and the capillary in the papillary process. In addition, it is difficult to measure a change in the papilla structure and the capillary in the papillary process over time at the same observation position or to appropriately investigate or diagnose the change and influence of other parts while appropriately checking the accurate number and shape of papillary structures and capillaries in a non-invasive manner.

Accordingly, an object of the invention is to provide an imaging apparatus, an image display system, and an image display method that can solve the problems of the invasive and non-invasive observation methods according to the related art and can observe both a papillary structure and a capillary in a papillary process at the same time.

According to the invention, there is provided an imaging apparatus comprising: an illumination unit that irradiates a surface of a skin with illumination light; an imaging unit that captures transmitted light reflected from the inside of the skin; a light shielding unit that is brought into close contact with the surface of the skin, is used, and is provided so as to prevent light reflected from the surface of the skin from reaching the imaging unit; and a pressing unit having a distal end that presses the surface of the skin in order to curve an epidermis of the skin through which the transmitted light to be captured passes.

Preferably, the light shielding unit has a tubular shape and is opened in a normal direction to a sensor surface of the imaging unit.

Preferably, the light shielding unit has a cylindrical shape.

Preferably, the illumination unit emits the illumination light such that the surface of the skin is illuminated in a ring shape.

Preferably, the pressing unit is provided at a distal end of the light shielding unit and is formed as a first light shielding member that is integrated with the light shielding unit.

The pressing unit has a tubular shape with the same inside diameter as that of the light shielding unit and is opened in the normal direction to the sensor surface of the imaging unit.

The pressing unit may have a pressing unit main body and a pressing member that is attached to the pressing unit main body and directly presses the surface of the skin. The illumination unit may have an illumination unit main body from which the illumination light is emitted and a second light shielding member that is attached to the illumination unit main body and is provided on an outer circumferential side of the pressing member. The pressing unit main body and the illumination unit main body may be integrated to form a main body of the imaging apparatus. The pressing member and the second light shielding member may form an adapter that is attached to a distal end portion of the main body. The pressing member may have a conic nozzle shape having a circular through hole therein. The second light shielding member may have a cylindrical shape with an inside diameter greater than a maximum outside diameter of the pressing member. The pressing member and the second light shielding member may form a ring-shaped light guide slit that guides the illumination light emitted from the illumination unit main body to the surface of the skin between an outer circumferential surface of the pressing member and an inner circumferential surface of the light shielding member.

The distal end of the pressing unit protrudes from a distal end of the illumination unit. Preferably, a distance between a close contact surface between the illumination unit and the surface of the skin and a close contact surface between the pressing unit and the surface of the skin in the normal direction to the sensor surface of the imaging unit is in a range of 0.1 mm to 1.0 mm.

Preferably, a distance between an optical axis of the illumination light emitted from the illumination unit and an optical axis of the transmitted light received by the imaging unit in a horizontal direction of the sensor surface of the imaging unit is in a range of 0.5 mm to 50 mm.

Preferably, the illumination unit includes a plurality of light sources and the plurality of light sources are symmetrically arranged.

Preferably, the light source is an LED, an incandescent lamp, a fluorescent lamp, or a discharge lamp.

Preferably, the illumination unit further includes a cylindrical second light shielding member with an inside diameter larger than an outside diameter of the pressing unit. Preferably, the second light shielding member is provided on an outer circumferential side of the pressing unit. Preferably, a ring-shaped light guide slit is formed between an outer circumferential surface of the pressing unit and an inner circumferential surface of the second light shielding member. The illumination light may be emitted from the light sources to the surface of the skin through the light guide slit.

The illumination unit may further include an optical fiber cable and the illumination light may be emitted from the light sources to the surface of the skin through the optical fiber cable.

Preferably, the illumination unit comprises a transparent cover member provided in a portion that comes into contact with the surface of the skin.

Preferably, the imaging unit includes an objective lens.

According to the invention, there is provided an image display system comprising the imaging apparatus according to the invention and a display device that displays an image acquired by the imaging unit.

The image display system may further comprise an image processing apparatus that performs image processing on the basis of the image acquired by the imaging unit of the imaging apparatus. The display device may display an image processed by the image processing apparatus.

Preferably, the display device displays an RGB image and the RGB image includes an image corresponding to a papillary structure and a capillary in a papillary process.

Preferably, the RGB image further includes an image corresponding to a reticular layer blood vessel.

Preferably, the RGB image includes a looped brown portion and a looped red portion surrounded by the looped brown portion.

Preferably, the looped brown portion is a melanin pigment included inside the skin and the looped red portion surrounded by the looped brown portion is the capillary in the papillary process.

According to the invention, there is provided an image display method using the image display system according to the invention. The image display method comprises: a first irradiation step of pressing a surface of a skin in order to curve an epidermis of the skin through which transmitted light to be captured passes and irradiating the surface of the skin with illumination light; a first image signal acquisition step of capturing only transmitted light reflected from the inside of the skin to acquire a first image signal of the skin whose epidermis has been curved; a first image formation step of forming an image of the skin whose epidermis has been curved on the basis of the first image signal; and an image display step of displaying the image of the skin whose epidermis has been curved on a monitor.

Preferably, the image display method further comprises: a second irradiation step of irradiating the surface of the skin with illumination light; a second image signal acquisition step of capturing only the transmitted light reflected from the inside of the skin to acquire a second image signal of the skin whose epidermis has not been curved in the same region as that including a position where the image of the skin whose epidermis has been curved is captured; a second image formation step of forming an image of the skin whose epidermis has not been curved on the basis of the second image signal; and an image display step of displaying the image of the skin whose epidermis has been curved and the image of the skin whose epidermis has not been curved on the monitor.

Preferably, in the first image formation step, a first RGB image of the skin whose epidermis has been curved is formed on the basis of the first image signal. Preferably, in the second image formation step, a second RGB image of the skin whose epidermis has not been curved is formed on the basis of the second image signal. Preferably, in the image display step, the first RGB image and the second RGB image are displayed on the monitor at the same time. Preferably, the first and second RGB images include an image corresponding to a papillary structure and a capillary in a papillary process.

The first RGB image and the second RGB image include a looped brown portion and a looped red portion surrounded by the looped brown portion. The looped brown portion is a melanin pigment included inside the skin and the looped red portion surrounded by the looped brown portion is the capillary in the papillary process. The second image signal related to the looped red portion acquired in the second image signal acquisition step is weaker than the first image signal related to the looped red portion acquired in the first image signal acquisition step.

In the second image formation step, the second RGB image may be formed on the basis of the second image signal weaker than the first image signal related to the looped red portion acquired in the first image signal acquisition step.

According to the invention, it is possible to easily observe both a papillary structure and a capillary in a papillary process in a non-invasive manner at the same time.

Since it is possible to non-invasively visualize a structure in the skin, it is possible to measure a change in the papillary structure or the capillary in the papillary process at the same observation position (that is, a collection target position) over time or to investigate the change or influence of other parts associated with the change in detail.

In addition, it is possible to appropriately observe the capillary in the papillary layer (papillary process) regardless of observation conditions, without breaking the capillary.

Further, it is possible to clearly distinguish and observe the capillary in the papillary process and the blood vessel in the reticular layer.

DESCRIPTION OF THE PREFERRED EMBODIMENTS

Hereinafter, embodiments of the invention will be described with reference to the accompanying drawings.

Embodiment 1

Figure 1A:
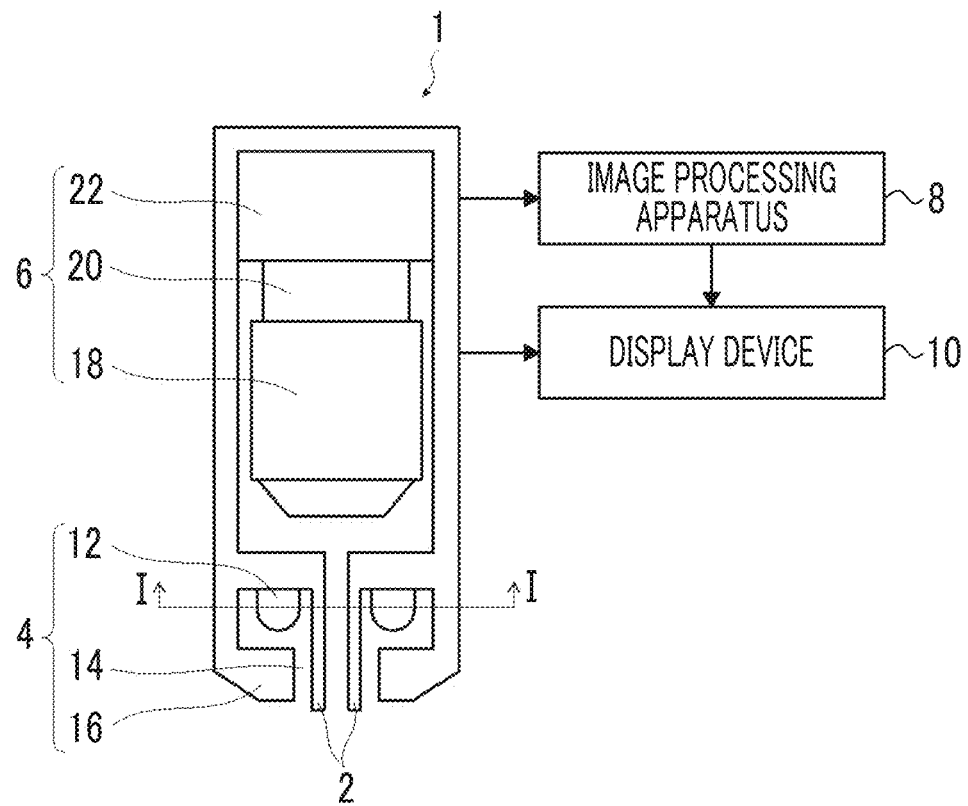
FIG. 1A is a cross-sectional view schematically illustrating an image display system using an imaging apparatus according to Embodiment 1 of the invention.
Figure 1B:
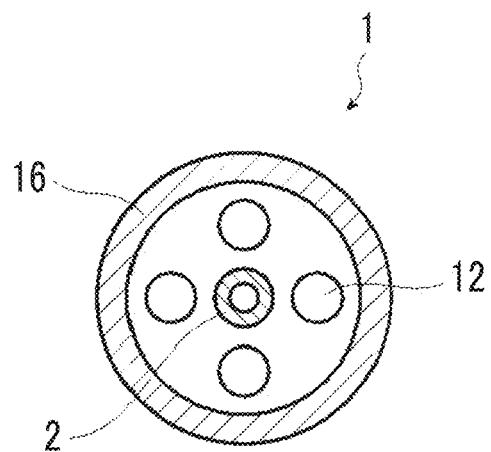
FIG. 1B is a cross-sectional view illustrating the imaging apparatus illustrated in FIG. 1A taken along the line I-I.

FIG. 1A is a cross-sectional view schematically illustrating an image display system using an imaging apparatus according to Embodiment 1 of the invention and FIG. 1B is a cross-sectional view illustrating the imaging apparatus illustrated in FIG. 1A taken along the line I-I.

Figure 2A:
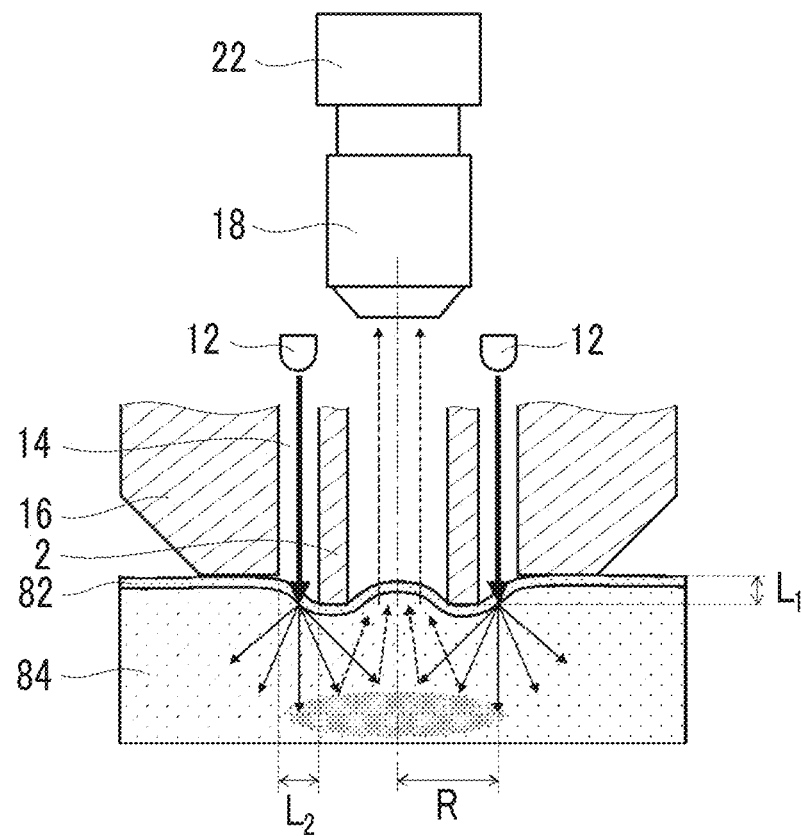
FIG. 2A is a cross-sectional view schematically illustrating an optical path of the imaging apparatus illustrated in FIG. 1A.
Figure 2B:
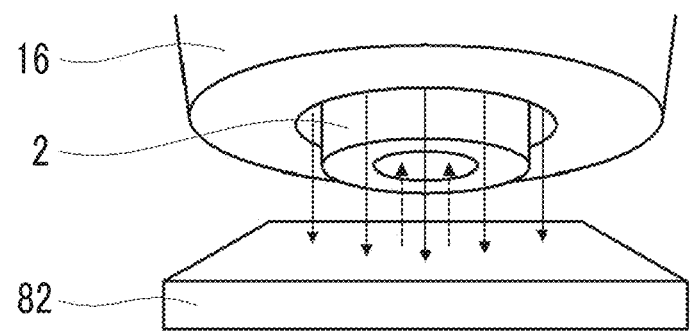
FIG. 2B is a cubic diagram illustrating an optical path at the distal ends of a pressing unit and an illumination unit of the imaging apparatus illustrated in FIG. 1A.

FIG. 2A is a cross-sectional view schematically illustrating an optical path of an imaging apparatus 1 according to Embodiment 1 and FIG. 2B is a cubic diagram illustrating an optical path at the distal ends of a pressing unit 2 and an illumination unit 4 of the imaging apparatus 1.

The imaging apparatus 1 includes the pressing unit 2, the illumination unit 4, and an imaging unit 6 and is connected to an image processing apparatus 8 and a display device 10.

The pressing unit 2 includes a cylindrical pressing member. In a state in which a distal end portion (an opening portion on the light receiving side) of the pressing unit 2 is brought into close contact with the surface of the skin such that a circular observation part (the surface of the skin captured by the imaging unit 6) is located in the diameter, the pressing unit 2 is pressed to curve the surface of the skin of the observation part. In addition, the distal end portion of the pressing unit 2 has a function of pressing the surface of the skin and functions as a light shielding member (first light shielding member) which shields light such that irradiation light emitted from the illumination unit 4, which will be described below, to the surface of the skin or specularly reflected light from the surface of the skin is not directly incident on the imaging unit 6. That is, the pressing unit 2 has a structure in which the pressing member is provided at the distal end of the light shielding member and the light shielding member and the pressing member (first light shielding member) are integrated.

In this embodiment, the pressing unit 2 has both of a pressing function and a light shielding function. However, the functions of the pressing unit 2 are limited thereto as long as the pressing unit 2 can press the surface of the skin such that blood is sent into a capillary in a papillary process. For example, the pressing member that presses the surface of the skin and the light shielding member (first light shielding member) used in close contact with the skin may be separately provided.

The size of the inner diameter of the pressing unit 2 (specifically, the diameter of a view field ring) is not particularly limited as long as an observation target can be easily searched. Preferably, the pressing unit 2 has an inside diameter that is slightly larger than the inside diameter at which it is easy to search for the observation target at the time of normal observation (that is, in a case in which the observation target is observed without being pressed). This is because the skin located inside the view field ring (that is, the skin in close contact with the pressing member) is deformed at the time of pressing. Specifically, the diameter of the view field ring is preferably in the range of 1 mm to 10 mm. The reason is as follows. In a case in which the diameter is less than 1 mm, the view field is too narrow and it is difficult to search for the observation target. On the other hand, in a case in which the diameter is greater than 10 mm, a light transmission distance illustrated in FIG. 3 which will be described below is long and attenuation occurs. As a result, a part in the view field looks dark.

Further, the size of the outer diameter is not particularly limited as long as the pressing unit 2 has a thickness and strength capable of pressing the surface of the skin, the amount of light in the view field can be uniformly and sufficiently ensured, and a contact width with the surface of the skin (that is, the difference between the outer diameter and the inner diameter of the pressing unit 2) is a value at which the capillary in the papillary process is not forcibly pressed. It is preferable to appropriately set the thickness or material of the pressing unit 2. For example, in a case in which the pressing unit 2 has a thickness of 0.5 mm and is made of rubber, the size of the outside diameter is preferably in the range of 2 mm to 11 mm.

The material forming the pressing unit 2 is not particularly limited as long as the distal end portion can be brought into close contact with the surface of the skin so as to prevent illumination light and reflected light from the surface of the skin from reaching the imaging unit 6. It is preferable to use a material which is not largely deformed in shape (that is, harder than the skin) in a case in which the pressing unit 2 presses the surface of the skin and is soft enough to fit more closely with the surface of the skin. For example, it is preferable to use an elastic material such as silicone rubber. In this case, it is possible to prevent the leakage of illumination light and reflected light from a light guide slit 14.

In addition, it is preferable that the distal end portion of the pressing unit 2 coming into contact with the skin has a slightly rounded shape in terms of safety.

The illumination unit 4 includes four light sources 12 and a light shielding member (second light shielding member) 16. The light shielding member (second light shielding member) 16 and the pressing unit (first light shielding member) 2 form the light guide slit 14. As illustrated in FIG. 2B, the illumination unit 4 emits light from the light sources 12 through the light guide slit 14 such that the surface of the skin is illuminated in a ring shape.

The four light sources 12 are four light-emitting diodes (LEDs) which are arranged on the same circumference so as to be symmetric with respect to a point. However, the light sources are not particularly limited as long as they can uniformly illuminate the surface of the skin through the light guide slit 14 in a ring shape. Therefore, the light sources are not limited to the LEDs. For example, a laser diode (LD), a semiconductor laser, a lamp, such as a xenon lamp, and a superluminescent diode (SLD) may also be used. The number of light sources is not particularly limited as long as the light sources can uniformly illuminate the surface of the skin with brightness required for the imaging unit 6 to capture the image of the surface of the skin. The number of light sources may be one as long as the light sources can concentrically illuminate the surface of the skin. The number of light sources is preferably two or more and more preferably four or more.

The intensity of the light source is not particularly limited as long as the view field of a region related to the observation part is bright enough for the imaging unit 6 to capture images. Preferably, the intensity of the light source can be adjusted.

The color of the light source is not particularly limited as long as it is not a single color of red (R) and blue (B) and includes green (G). It is preferable to use RGB (red-green-blue) light (that is, white light) and GB (green-blue) light. In addition, it is preferable that the color of the light source is switched to each color.

A power supply for the light sources may be an internal power supply (battery) or an external power supply.

The light shielding member 16 is a cylindrical member having an inside diameter larger than the outside diameter of the pressing unit 2 and is disposed on the outer circumferential side of the pressing unit 2 with a cylindrical shape. The light guide slit 14 with a ring shape is formed between an outer circumferential surface of the pressing unit 2 and an inner circumferential surface of the light shielding member 16. As illustrated in FIG. 1A, a distal end portion (an opening portion on the light emission side) of the light shielding member 16 is located slightly behind the distal end portion (the opening portion on the light receiving side) of the pressing unit 2. In other words, the pressing unit 2 protrudes from the distal end portion of the light shielding member 16 of the illumination unit 4.

The distal end portion (the opening portion on the light receiving side) of the pressing unit 2 protrudes from the distal end portion (the opening portion on the light emission side) of the light shielding member 16. The amount of protrusion (that is, a distance $L_1$ from a close contact surface between the light shielding member 16 and the surface of the skin to a close contact surface between the pressing unit 2 and the surface of the skin) can be set according to the amount of deformation of the skin at the time of pressing (the depth of a recess generated in the skin in a case in which the skin is pressed).

For example, since the amount of deformation of a thin portion (for example, the back of the hand) of the human skin at the time of pressing is about 1 mm, the amount of protrusion ($L_1$) is preferably set in the range of 0.1 mm to 1.0 mm which is less than the amount of deformation. The reason is as follows. A length of 0.1 mm or more is required to curve the epidermis in a case in which the eye rim or the back of the hand is pressed. In a case in which the amount of protrusion is equal to or less than 1.0 mm and the imaging device 1 is placed on the surface of the skin and the pressing unit 2 is pressed against the surface of the skin with a required pressure, it is easy to bring the distal end portion of the light shielding member 16 into close contact with the surface of the skin, without forcibly pressing the surface of the skin.

The weight of the imaging apparatus 1 is not particularly limited as long as it does not damage the capillaries (for example, 1 kg) in a case in which the imaging device 1 is placed on the surface of the skin and is preferably in the range of 50 g to 600 g. In a case in which the distal end portions of the pressing unit 2 and the light shielding member 16 of the imaging apparatus 1 come into close contact with the surface of the skin, this weight range makes it possible to compress the blood vessels in the reticular layer without damaging the capillaries.

With this arrangement configuration, as illustrated in FIG. 2A, in a case in which the imaging device 1 is placed on the surface of the skin to be observed, the distal end portion of the light shielding member 16 and the distal end portion of the pressing unit 2 are brought into close contact with the surface of the skin by the weight of the imaging apparatus 1 and the surface of the skin is pressed by the pressing unit 2 with required pressure. As such, in a case in which the distal end portion of the light shielding member 16 and the distal end portion of the pressing unit 2 are brought into close contact with the surface of the skin and the surface of the skin is irradiated with light, it is possible to prevent a reduction in the intensity of transmitted light and a reduction in the contrast of a captured image. Here, the transmitted light is light which has been transmitted through the surface of the skin, reflected from the inside of the skin, and transmitted again through the surface of the skin. The reduction in the contrast of the captured image is caused by the capture of the light reflected from the surface of the skin in addition to the transmitted light.

The outside diameter of the light shielding member 16 is not particularly limited as long as the contact area of the distal end portion with the surface of the skin is enough to prevent the illumination light from leaking from the light guide slit 14. It is preferable that the outside diameter is set so as not to hinder the placement of the imaging apparatus 1 on the surface of the skin.

The material forming the light shielding member 16 is not particularly limited as long as the distal end portion can be brought into close contact with the surface of the skin such that the illumination light is not diffused. However, the light shielding member 16 can be formed in a shape that fits more closely to the surface of the skin and is slightly rounded. For example, it is preferable to use an elastic material such as silicone rubber. In this case, it is possible to prevent the leakage of the illumination light from the light guide slit 14.

The light emitted from the light source 12 is diffused by the light guide slit 14 and is then transmitted in the light guide slit 14. Since the surface of the skin is irradiated with the light emitted from the light source 12 through the light guide slit 14, the diffusion width of light is less than the width of the light guide slit 14 and the surface of the skin can be directly illuminated with the light.

The width $L_2$ (the difference between the inside diameter of the light shielding member 16 and the outside diameter of the pressing unit 2) of the light guide slit 14 is not particularly limited as long as the brightness of the view field capable of checking an observation target, such as capillaries, can be ensured. Since an object of the invention is to observe the papillary structure or the capillary in the papillary process, it is preferable that the light shielding member 16 has a width of 1.0 mm to 5.0 mm at which the blood vessels can be easily searched.

The light guide slit 14 makes it possible to use, for example, a general LED or lamp as the light source 12 and has the effect that the size is hardly limited. Specifically, as illustrated in FIG. 8B which will be described below, a light source with a size greater than a ring-shaped space (corresponding to the light guide slit 14) between the outer circumferential surface of the pressing unit 2 and the inner circumferential surface of the light shielding member 16 may be used. In addition, it is possible to ensure a sufficient amount of light and uniformity.

In addition, the processing of the light shielding member (second light shielding member) 16 and the pressing unit (first light shielding member) 2 of the illumination unit 4 is easier than that in a case in which an optical fiber illustrated in FIG. 8D (which will be described below) that is difficult to process is used. Therefore, it is possible to obtain the effect of generating ring-shaped illumination light that is emitted from a general light source 12 to the surface of the skin. Further, the light source according to this embodiment is provided in the apparatus unlike the configuration in which the light source is provided outside the apparatus and a thick cable (optical fiber cable) for connecting the light source and a bundle of optical fibers is required. Therefore, no cables are required and it is possible to reduce the overall size of the imaging apparatus.

The shape of the light guide slit 14 is not limited to the cylindrical shape (ring shape) and may be a tubular shape. That is, in this embodiment, the shape of the pressing unit 2 and the light shielding member 16 is a cylindrical shape. However, the shape is not particularly limited as long as the pressing unit 2 and the light shielding member 16 have a tubular shape. That is, the shape of the outer circumferential surface of the pressing unit 2 and the inner circumferential surface of the light shielding member are not particularly limited.

The imaging unit 6 includes an objective lens 18 that acquire the transmitted light reflected from the inside of the skin, a driving unit 20 that automatically or manually performs a focus operation of the objective lens 18, and a camera 22.

A single-focus lens can be used as the objective lens 18 and the driving unit 20 can automatically or manually adjust the focus function of the objective lens 18. In addition, the driving unit 20 may not be used and a zoom lens may be used as the objective lens 18.

The camera 22 is provided such that a sensor surface faces an observation part, captures the transmitted light reflected from the inside of the skin through the opening of the pressing unit 2 or the objective lens 18, and acquires an image signal of the skin. In addition, an image is generated on the basis of the acquired image signal.

Here, the optical path of the imaging apparatus 1 will be described in detail.

As illustrated in FIG. 2A, the surface of the skin is illuminated in a ring shape with light emitted from the light source 12 through the light guide slit 14 and the light is transmitted into the skin. The transmitted light entering the skin is diffused by the dermis and the epidermis or is reflected therefrom and returns from the inside of the skin. The light returning from the inside of the skin is transmitted through the surface of the skin, is incident on the inner cavity of the pressing unit 2, is transmitted through the pressing unit 2, and is capture by the camera 22 through the objective lens 18.

The distance (that is, the illumination radius R) between the optical axis (that is, the optical axis of light transmitted through the light guide slit 14) of the illumination light emitted from the light sources 12 arranged on the same circumference and the optical axis (that is, the central axis of the inner cavity of the pressing unit 2) of the transmitted light received by the objective lens 18 is not particularly limited as long as the brightness of the view field capable of checking the observation target can be ensured. It is preferable that the distance is set in the range of 0.5 mm to 50 mm. In a case in which the illumination radius is set to be less than 0.5 mm, it is difficult to search for the observation target. In a case in which the illumination radius is set to be greater than 50 mm, the view field becomes dark. Therefore, it is necessary to use a very strong light source. As a result, it is necessary to irradiate the skin with high-temperature light.

Figure 3:
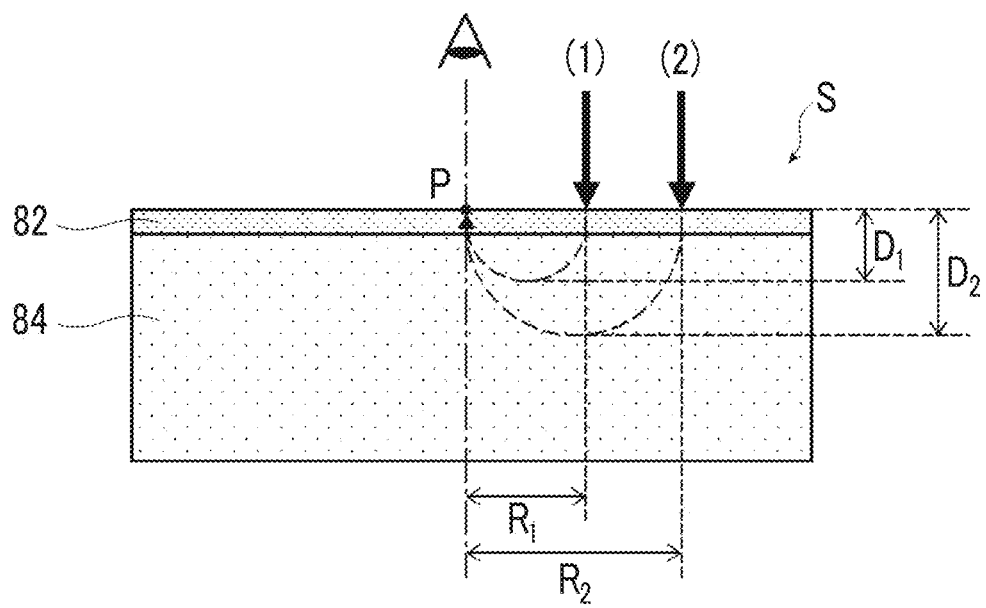
FIG. 3 is a diagram schematically illustrating an illumination radius R of the imaging apparatus illustrated in FIG. 1A.

Here, the operation of the illumination radius R will be described in detail with reference to FIG. 3.

In general, as a light incident position becomes further away from an observation point P, light is diffused inside the skin and the amount of light returning from the inside of the skin as internally diffused light or internally reflected light is reduced exponentially. For example, as illustrated in FIG. 3, the amount of light returning from the inside of the skin as the internally diffused light or the internally reflected light (a dotted line in FIG. 3) at a light incident position (2) (illumination radius $R_2$) farther away from the observation point than a light incident position (1) (illumination radius $R_1$) is reduced exponentially.

In addition, it is generally said that the length of the illumination radius and the maximum depth at which light incident on the inside of the skin reaches are equal to each other. That is, as the illumination radius becomes larger, light returns from a deeper position inside the skin. Therefore, it is possible to obtain information at a deep position.

Specifically, since the illumination radius $R_2$ is greater than the illumination radius $R_1$, light with the illumination radius $R_2$ at a maximum depth $D_2$ that is greater than a maximum depth $D_1$ can be used to obtain information at a deeper position inside the skin than light with the illumination radius $R_1$ at a maximum depth $D_1$.

Therefore, it is preferable to set the illumination radius R according to, for example, the intensity of the light source used, the size of an observation target, and the position of the observation target in the skin.

Since an object of the invention is to observe the papillary structure and the capillary in the papillary process, it is preferable to acquire information from the surface of the skin S to a region including an epidermis 82 and a dermis 84. Specifically, it is preferable to acquire information on a region that is 0.5 mm to 5 mm away from the surface of the skin S. It is more preferable to acquire information on a region that is 500 μm to 1000 μm away from the surface of the skin S. Therefore, theoretically, it is more preferable that the illumination radius is about 1 mm.

Since the preferred illumination radius depends on the color of the skin of the subject and the thickness of the epidermis and dermis of an observation part, it is preferable to adjust the illumination radius considering those conditions.

Figure 4:
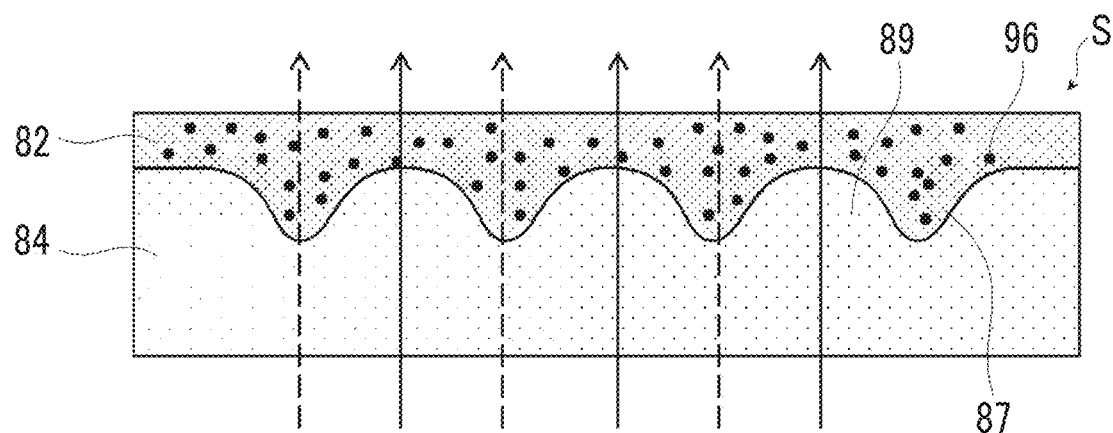
FIG. 4 is a diagram schematically illustrating the principle of visualizing a papillary structure.

Next, the principle of visualizing the papillary structure by capturing the image of the surface of the skin S using the imaging apparatus 1 will be described in detail with reference to FIG. 4.

Figure 5A:
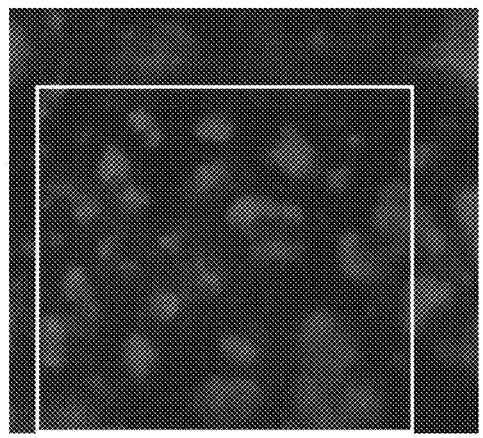
FIG. 5A illustrates a transmission image acquired by the imaging apparatus illustrated in FIG. 1A.
Figure 5B:
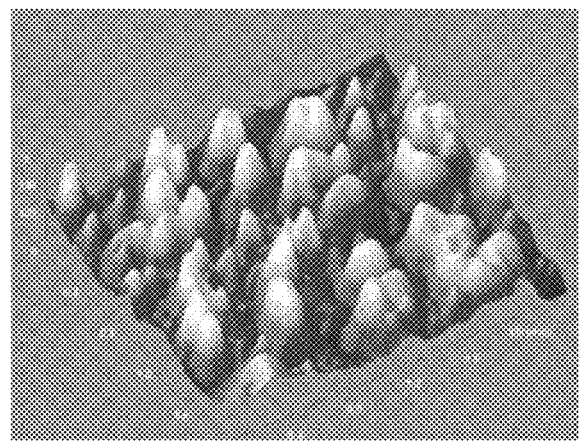
FIG. 5B is a cubic diagram illustrating a transmission image in a white frame illustrated in FIG. 5A.

FIG. 5A illustrates a transmission image (RGB image) obtained by capturing the transmitted light returning from the inside of the skin and FIG. 5B is a diagram three-dimensionally expressing the transmission image in a white frame of FIG. 5A.

Figure 14:
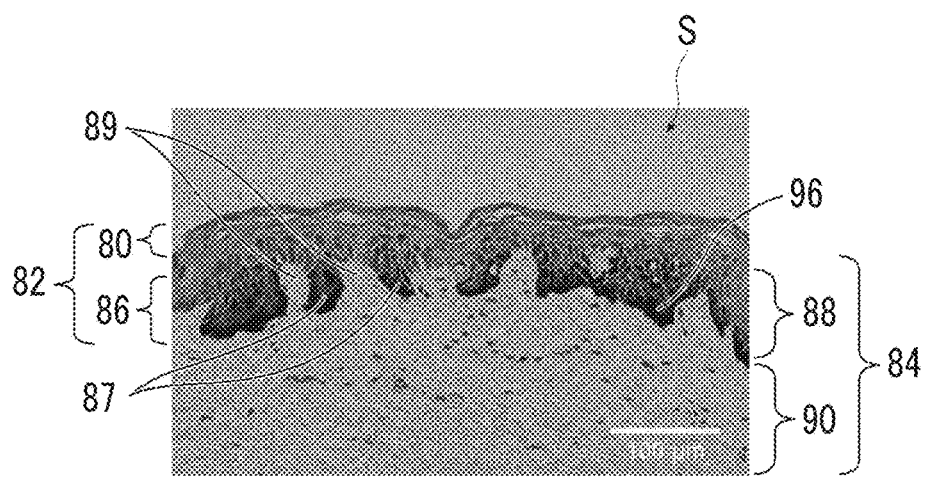
FIG. 14 illustrates an enlarged image of stained skin tissue pieces.
Figure 15:
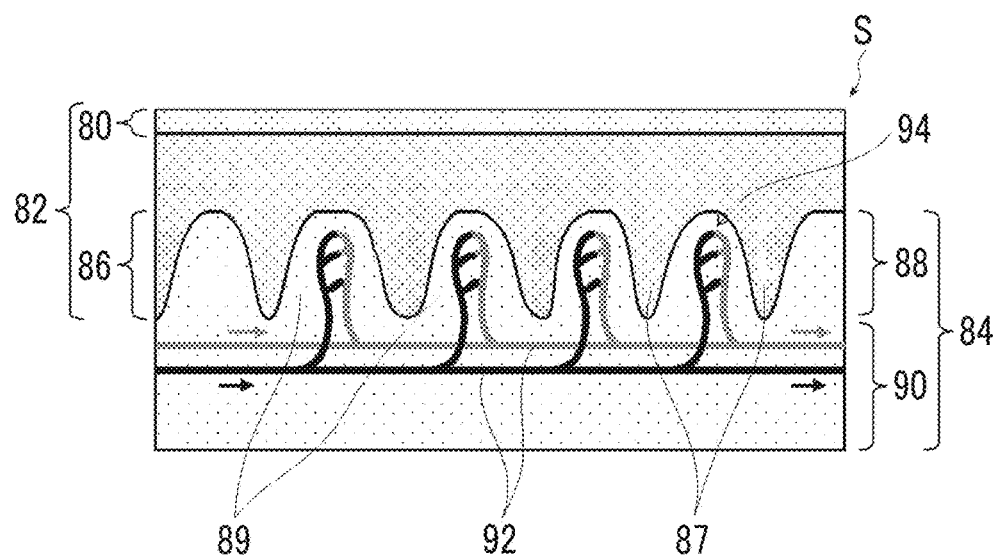
FIG. 15 is a diagram schematically illustrating the structure of a skin tissue.

A bright region in FIG. 5A and a bright convex region in FIG. 5B correspond to a shallow portion under the skin and a dark region in FIG. 5A and a dark concave region in FIG. 5B correspond to a deep portion under the skin. As illustrated in FIG. 4, a melanin pigment 96 included only in the epidermis 82 has an action of shielding light in a case in which the transmitted light returns from the side of the skin through the dermis 84 and the epidermis 82. The reason is that, as can be seen from a skin tissue image illustrated in FIG. 14, the melanin pigment 96 is black and a large number of melanin pigments 96 are present in the vicinity of the boundary between the epidermis 82 and the dermis 84. Therefore, it is considered that light (a solid arrow in FIG. 4) transmitted through a convex portion (papillary process 89) of a papillary layer 88 in which the epidermis 82 is thin is bright and light (a dotted arrow in FIG. 4) transmitted through a concave portion (and an epidermal process 87) of the papillary layer 88 in which the epidermis 82 is thick is bright.

Figure 6A:
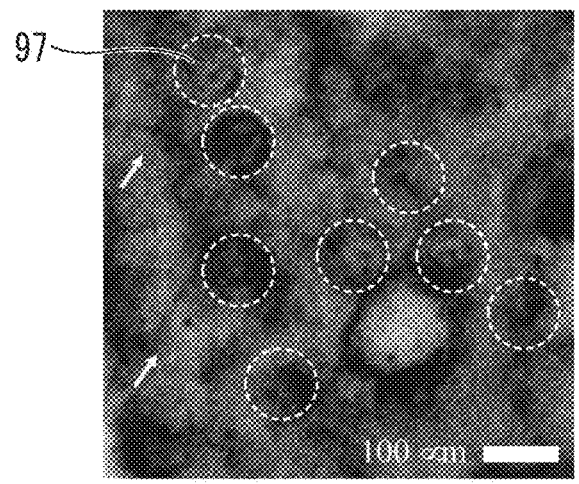
FIG. 6A is a diagram illustrating an RGB image (scale bar 100 μm) acquired by the imaging apparatus illustrated in FIG. 1A.
Figure 6B:
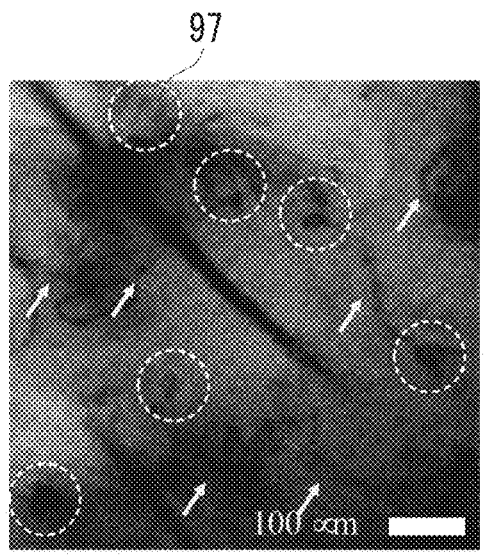
FIG. 6B is a diagram illustrating an RGB image (scale bar 100 μm) acquired by the imaging apparatus illustrated in FIG. 1A.
Figure 6C:
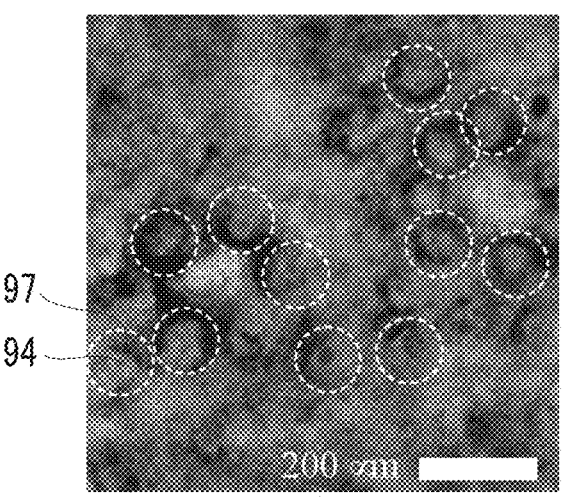
FIG. 6C is a diagram illustrating an RGB image (scale bar 200 μm) acquired by the imaging apparatus illustrated in FIG. 1A.
Figure 6D:
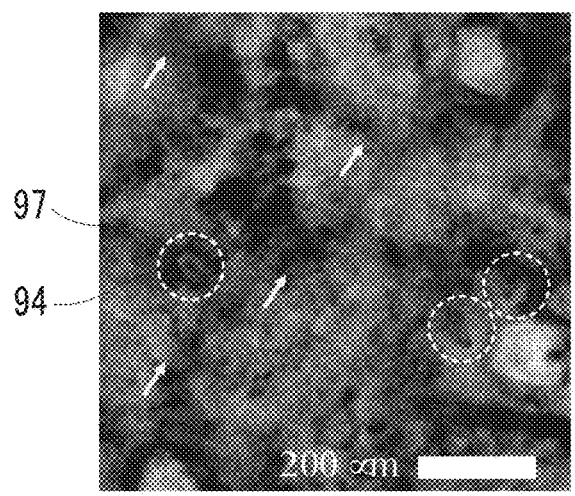
FIG. 6D is a diagram illustrating an RGB image (scale bar 200 μm) acquired by the imaging apparatus illustrated in FIG. 1A.

FIG. 6A is an RGB image (scale bar 100 μm) acquired by capturing the surface of the human cheek using the imaging apparatus 1 (the magnification of the objective lens is 4.5). FIG. 6B is an RGB image (scale bar 100 μm) acquired by capturing parts around the human eyes using the imaging apparatus 1. FIG. 6C is an RGB image (scale bar 200 μm) acquired by capturing the surface of the back of the human hand using the imaging apparatus 1. FIG. 6D is an RGB image (scale bar 200 μm) acquired by capturing the surface of the back of the human hand using the imaging apparatus 1.

As can be seen from FIGS. 6A to 6D, since a brown portion corresponds to a melanin pigment, a looped brown portion 97 is a recess in the papillary layer 88. Further, since a red portion corresponds to the blood vessel, a looped red portion 94 that is seen as a bright central portion present inside the looped brown portion 97 is the capillary in the papillary process.

Therefore, a portion surrounded by a dotted line corresponds to the papillary structure.

In addition, a red portion that is seen outside the papillary structure (a portion surrounded by a dotted line) represented by an arrow is the blood vessel in the reticular layer. Therefore, the capillaries 94 in the papillary process and the blood vessels in the reticular layer (reticular layer blood vessels) 92 can be clearly distinguished and observed.

It is difficult to distinguish the brown portion and the red portion in black-and-white images. However, in practice (that is, in RGB images), it is possible to clearly identify the difference between the brown portion and the red portion. In FIGS. 6A to 6D, it is possible to identify the concave portion 97 of the papillary layer as the looped brown portion inside the portion surrounded by the dotted line. In addition, in FIGS. 6C and 6D which are larger than FIGS. 6A and 6B in scale, it is possible to identify the capillary 94 in the papillary process as the looped red portion inside the looped brown portion. Further, it is possible to identify the reticular layer blood vessel 92 as the red portion represented by an arrow outside the portion surrounded by the dotted line.

As such, according to this embodiment, it is possible to appropriately observe the papillary structure or the capillary in the papillary process.

Figure 7A:
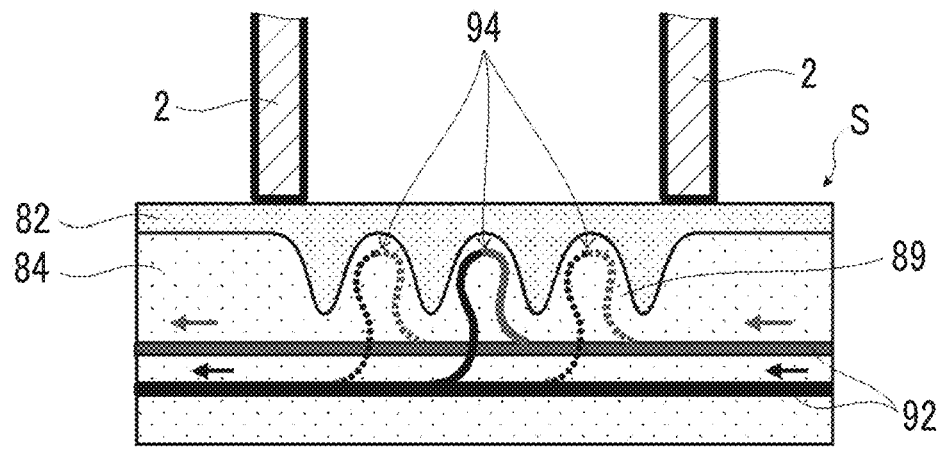
FIG. 7A is a diagram schematically illustrating a state before a surface of the skin is processed by the pressing unit.

Next, The pressing effect by the pressing unit 2 will be described in detail with reference to FIGS. 7A and 7B. FIG. 7A illustrates a state before the surface of the skin S is pressed by the pressing unit 2 and FIG. 7B illustrates a state in which the surface of the skin S is pressed by the pressing unit 2.

The capillaries in the skin are contracted and/or expanded to adjust a blood flow, thereby adjusting the body temperature. Therefore, as illustrated in FIG. 7A, in the state before the surface of skin S is pressed by the pressing unit 2, blood does not always flows in all of the capillaries in an observation region. As a result, there is a capillary that is not capable of being visually recognized in an observation image. Therefore, in the observation method according to the related art, it is necessary to continuously observe the observation region until blood circulates through all of the capillaries in the observation region. As a result, it takes a few minutes for the observation. In addition, it may be difficult to observe all capillaries over time.

Figure 7B:
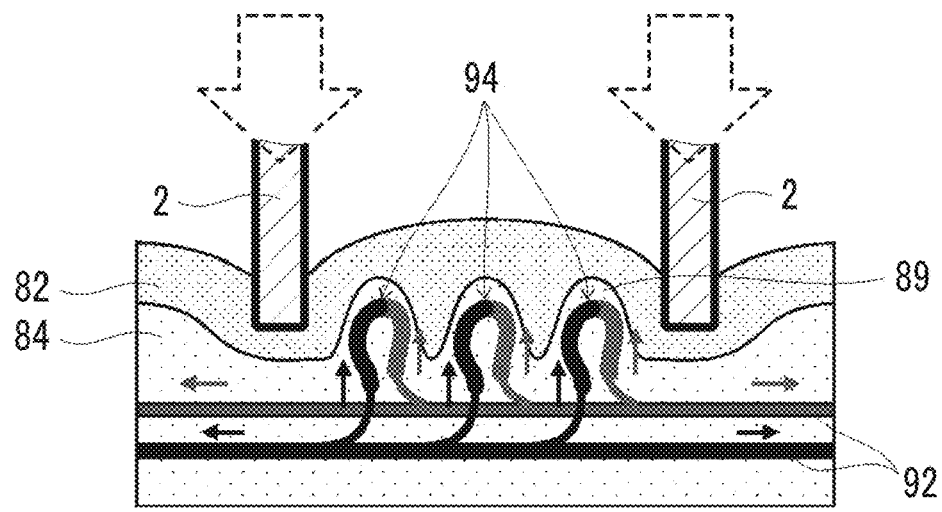
FIG. 7B is a diagram schematically illustrating a state in which the surface of the skin is processed by the pressing unit.

In contrast, as illustrated in FIG. 7B, in a case in which the surface of the skin in the vicinity of the observation region is pressed by the pressing unit 2, the blood vessels (reticular layer blood vessels) 92 in the vicinity of the observation region are pressed and blood is forcibly sent to the capillaries in the observation region. In other words, it is possible to acquire even an image signal of the capillary (the loop 94 of the capillaries in the papillary processes) which is too weak to be visible before pressing. As a result, it is possible to observe the capillaries in the observation image. In particular, immediately after the pressing unit 2 is pressed against the skin, this effect is obtained. Therefore, it is possible to observe the capillaries for about 10 seconds.

As such, according to this embodiment, since the skin in the vicinity of an observation part is pressed to compress the surrounding blood vessels, it is possible to detect the apex of the loop 94 of the capillaries in the papillary processes in the observation part, regardless of the observation conditions.

The image processing apparatus 8 includes, for example, a personal computer (PC), a central processing unit (CPU), a microprocessor unit (MPU) and performs image processing related to observation or diagnosis for a captured image input from the imaging unit 6. For example, the image processing apparatus 8 can generate a G component image on the basis of an RGB image input from the imaging unit 6. The G component image is suitable for searching for and observing capillaries since the contrast of the blood vessels (hemoglobin components) can be enhanced.

In addition, the image processing apparatus 8 includes a memory (not illustrated) and can store the generated processed image.

The display device 10 includes a display, such as a liquid crystal display (LCD), and displays the image captured by the imaging unit 6 or the image generated by the image processing apparatus 8 on a monitor. The images displayed on the monitor can be switched by the image processing apparatus 8. For example, in a case in which the user wants to observe the distribution of melanin pigments together with the capillaries after observing the capillaries in the G component image, the G component image can be switched to an RGB image. In the RGB image, the capillaries are displayed in red and the melanin pigments are displayed in brown. Therefore, it is possible to easily distinguish the capillaries and the melanin pigments.

In addition, the imaging apparatus 1 and the image processing apparatus 8 may have an output device such as a printer (not illustrated).

Next, the operation of the imaging apparatus 1 according to Embodiment 1 will be described.

First, after the imaging apparatus 1 is placed on the skin of the subject, as illustrated in FIG. 2A, the pressing unit 2 is pressed against the surface of the skin and the distal end portion of the light shielding member 16 and the pressing unit 2 are disposed so as to come into close contact with the surface of the skin. Then, the surface of the skin is irradiated with light emitted from the light source 12 through the light guide slit 14. The emitted light is transmitted through the skin. Light other than light absorbed by melanin distributed in the epidermis and hemoglobin in blood is scattered by the epidermis or the dermis and returns from the inside of the skin as diffused reflected light. The light returning from the inside of the skin is captured by the camera 22 through the objective lens 18. The image acquired by the imaging apparatus 1 is displayed on the monitor of the display device 10.

The image acquired by the imaging apparatus 1 may be processed by the image processing apparatus 8 and then displayed on the display device 10.

In a case in which an image is acquired by the imaging apparatus 1 according to Embodiment 1 and is then displayed on the monitor of the display device 10, the following observation and evaluation can be performed. In addition, in a case in which the image processed by the image processing apparatus 8 is displayed on the monitor of the display device 10, the following observation and evaluation can be performed.

For example, since the images of the capillaries in the papillary processes of the skin in each part of the human body can be appropriately acquired, it is possible to accurately compare the number density of the capillaries between the parts. In addition, it is possible to evaluate a difference in the number density of the capillaries in each part due to a difference in the age of the subject (for example, aging).

Further, since the image of the inside of the skin can be obtained non-invasively, it is possible to observe a change in the capillary in the papillary process at the same subject and at the same observation position over time in units of several days to several years.

In addition, since the thickness of the blood vessel can be recognized from the image, it is possible to accurately evaluate a blood flow rate. Furthermore, since the capillary in the papillary process and the blood vessels in the reticular layer can be clearly distinguished and recognized from the image, it is also possible to evaluate the difference between the blood flows in the capillaries and the blood vessels.

Further, the imaging apparatus 1 can acquire a moving image as well as a still image. Therefore, for example, it is possible to observe a change in the capillary in the papillary process and the blood vessels in the reticular layer which occurs in a case in which the subject takes a medicine over time.

It is possible to evaluate a difference in blood flow by comparing an image (that is, an image including a melanin pigment and a capillary in the papillary process) acquired in a state in which the pressing unit 2 is pressed against the surface of the skin with an image (that is, an image including only a melanin pigment or an image including the capillary in the papillary process based on an image signal which is too weak to be invisibly recognized as a melanin pigment) acquired in a state in which the pressing unit 2 is not pressed.

In addition, since the image of the papillary structure of the skin in each part of the human body can be appropriately acquired, it is possible to appropriately compare a difference in the papillary structure in each part.

Specifically, it is possible to evaluate a difference in the number density and flatness (the unevenness of the papillary layer formed by the epidermal process 87 and the papillary process 89) of the papillary process between the parts.

Similarly to the capillary in the papillary process, it is possible to observe a change in the papillary structure in the same subject and at the same observation position over time in units of several days to several years.

A melanin pigment can also be clearly recognized from the image. Therefore, for freckles and pigmentation, it is also possible to observe a change in the papillary structure in the same subject and at the same observation position over time in units of several days to several years.

As such, since the papillary structure and the capillary in the papillary process can be simultaneously observed at the same time, it is possible to appropriately evaluate the state of the skin and to appropriately recognize a change in the skin due to aging. As a result, it is possible to check the effects of cosmetics, skin care products, and skin care. Therefore, this configuration can be applied to the research of cosmetics or the development of goods.

In Embodiment 1, the surface of the skin is illuminated with light emitted from four light sources 12, which are concentrically arranged so as to be symmetrical with each other, through the light guide slit 14. However, the invention is not limited thereto. The size, number, and arrangement position of the light sources may be changed or the configuration of the light guide slit may be changed.

FIGS. 8A to 8E illustrate modification examples of the illumination unit 4 of the imaging apparatus 1 according to Embodiment 1.

Modification Example 1 of Embodiment 1

Figure 8A:
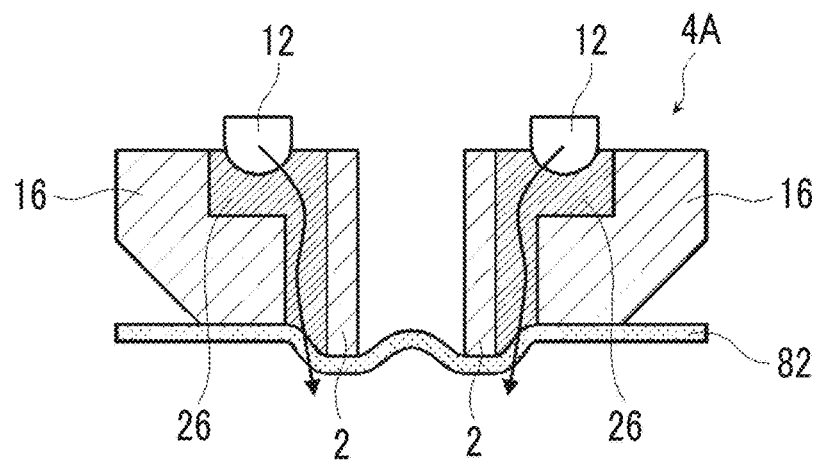
FIG. 8A is a diagram schematically illustrating Modification Example 1 of the illumination unit of the imaging apparatus illustrated in FIG. 1A.
Figure 8B:
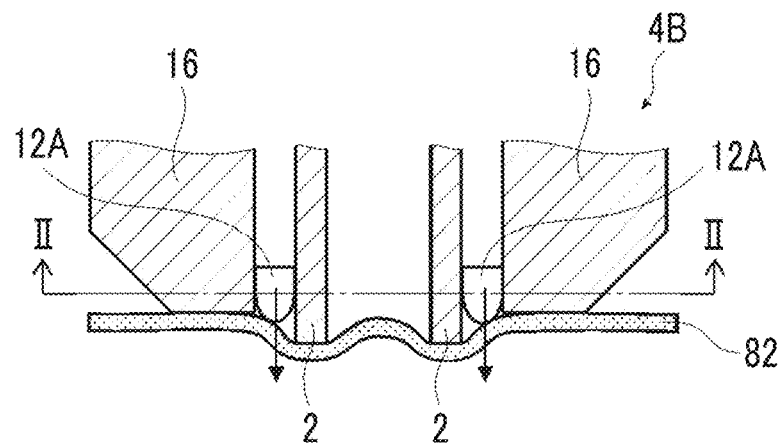
FIG. 8B is a diagram schematically illustrating Modification Example 2 of the illumination unit of the imaging apparatus illustrated in FIG. 1A.

FIG. 8A is a cross-sectional view illustrating an illumination unit according to Modification Example 1 of Embodiment 1.

An illumination unit 4A illustrated in FIG. 8A includes a ring-shaped light guide member 26 formed by filling a ring-shaped space (corresponding to the light guide slit 14) between an outer circumferential surface of the pressing unit 2 and an inner circumferential surface of the light shielding member 16 with a light transmitting resin that refracts light, instead of the light guide slit 14 of the illumination unit 4 in the imaging apparatus 1 according to Embodiment 1 illustrated in FIGS. 1A and 1B.

The resin filling the light guide slit is not particularly limited as long as it is transparent, is easy to process, and is generally used as a material forming an optical fiber.

According to the light guide member 26, it is possible to reduce the loss of light even in a case in which the size of the light source 12 is small and to ensure a sufficient amount of light in the view field.

Modification Example 2 of Embodiment 1

Figure 8C:
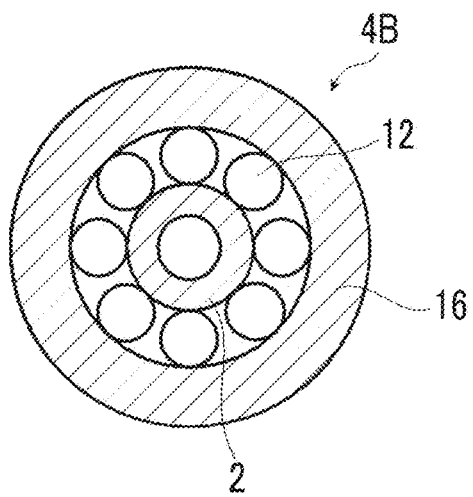
FIG. 8C is a cross-sectional view illustrating an imaging apparatus illustrated in FIG. 8B taken along the line II-II.

FIG. 8B is a cross-sectional view illustrating an illumination unit according to Modification Example 2 of Embodiment 1. FIG. 8C is a cross-sectional view illustrating the illumination unit illustrated in FIG. 8B taken along the line II-II.

An illumination unit 4B illustrated in FIGS. 8B and 8C includes eight light sources 12A, instead of the four light sources 12 of the illumination unit 4 in the imaging apparatus 1 according to Embodiment 1 illustrated in FIGS. 1A and 1B. The eight light sources 12A are symmetrically arranged in a concentric shape at the distal end of a ring-shaped space (corresponding to the light guide slit 14) between the outer circumferential surface of the pressing unit 2 and the inner circumferential surface of the light shielding member 16 such that the ends of the light sources come into close contact with the surface of the skin.

As such, according to the illumination unit 4A in which the number of light sources increases and the ends of the light sources 12A come into close contact with the surface of the skin, it is possible to ensure a sufficient amount of light in the view field and to further uniformize the brightness of the view field.

In addition, the illumination unit 4A may have a transparent cover member between the light sources 12A and the surface of the skin. Examples of the material forming the transparent cover member include plastic and glass.

Modification Example 3 of Embodiment 1

Figure 8D:
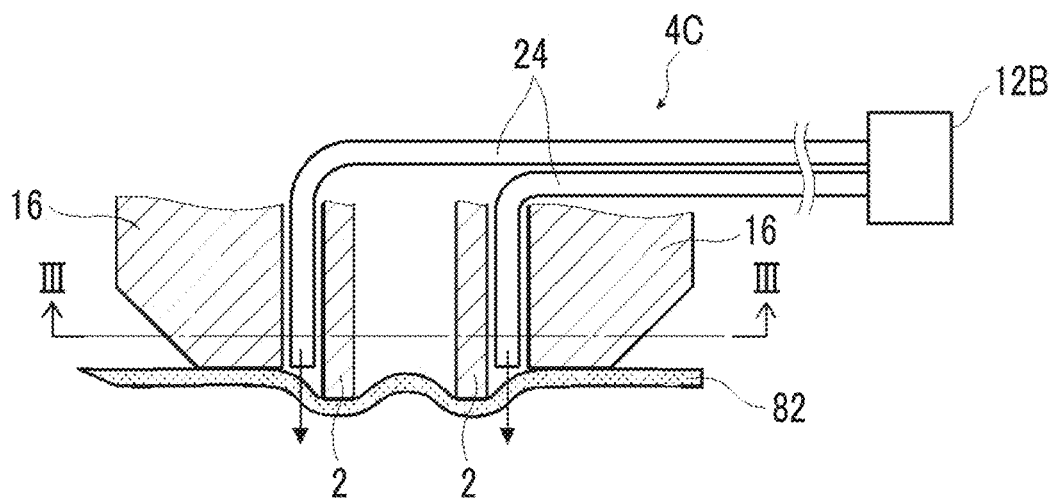
FIG. 8D is a diagram schematically illustrating Modification Example 3 of the illumination unit of the imaging apparatus illustrated in FIG. 1A.
Figure 8E:
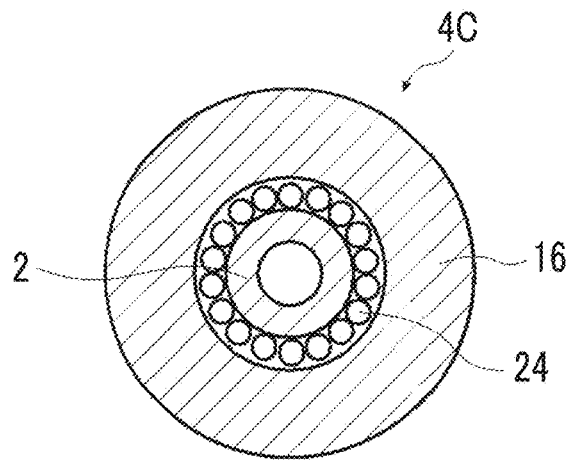
FIG. 8E is a cross-sectional view illustrating an imaging apparatus illustrated in FIG. 8D taken along the line III-III.

FIG. 8D is a cross-sectional view illustrating an illumination unit according to Modification Example 3 of Embodiment 1. FIG. 8E is a cross-sectional view illustrating the illumination unit illustrated in FIG. 8D taken along the line III-III.

An illumination unit 4C illustrated in FIGS. 8D and 8E further includes a plurality of optical fibers 24 that are connected to a light source 12B provided outside the housing of the imaging apparatus 1 according to Embodiment 1 illustrated in FIGS. 1A and 1B and are provided in a ring-shaped space (corresponding to the light guide slit 14) between the outer circumferential surface of the pressing unit 2 and the inner circumferential surface of the light shielding member 16.

The diameter of the distal end of the optical fiber 24 can be reduced and the diameter of the optical fiber 24 is less than that in, for example, LED illumination. Therefore, a plurality of optical fibers 24 can be uniformly arranged in the ring-shaped space (corresponding to the light guide slit 14) between the outer circumferential surface of the pressing unit 2 and the inner circumferential surface of the light shielding member 16. In addition, since the light source 12B provided outside the imaging apparatus 1 is used, it is possible to easily adjust the intensity or color of light.

Embodiment 2

In Embodiment 1, the integrated pressing unit 2 or the integrated illumination unit 4 which is not removable is used. However, the invention is not limited thereto. Only the distal end portion from which irradiation light is emitted to the surface of the skin and which receives light returning from the inside of the skin may be a replaceable adapter.

In addition, in Embodiment 1, the diameter of the view field ring of the pressing unit 2 or the width of the light guide slit of the illumination unit 4 is a predetermined value. However, the invention is not limited thereto. However, an adapter including a pressing unit in which the diameter of only the distal end portion of the view field ring is different or an illumination unit in which the width of only the distal end portion of the light guide slit is different may be used.

In Embodiment 1, the outside diameter of the light shielding member 16 is a predetermined value. However, adapters including light shielding members with different outside diameters may be used.

Figure 9:
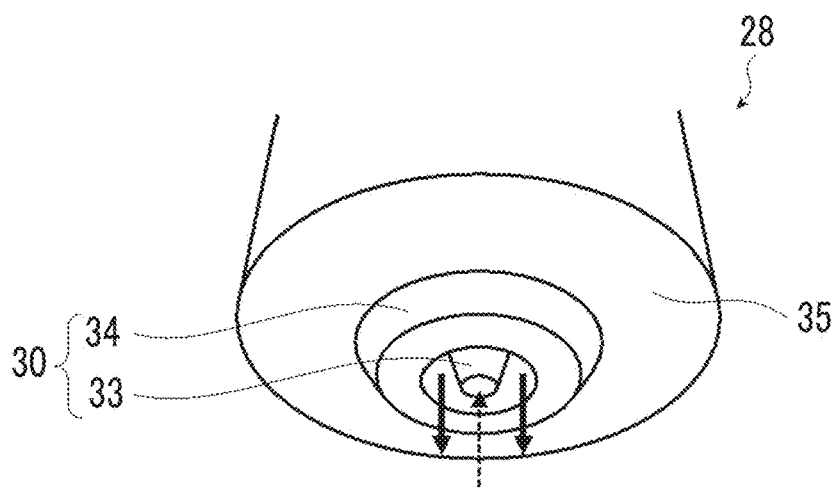
FIG. 9 is a cubic diagram illustrating an adapter of an imaging apparatus according to Embodiment 2 of the invention.

FIG. 9 illustrates an adapter 30 which is attached to a main body 28 of an imaging apparatus according to Embodiment 2.

Figure 10:
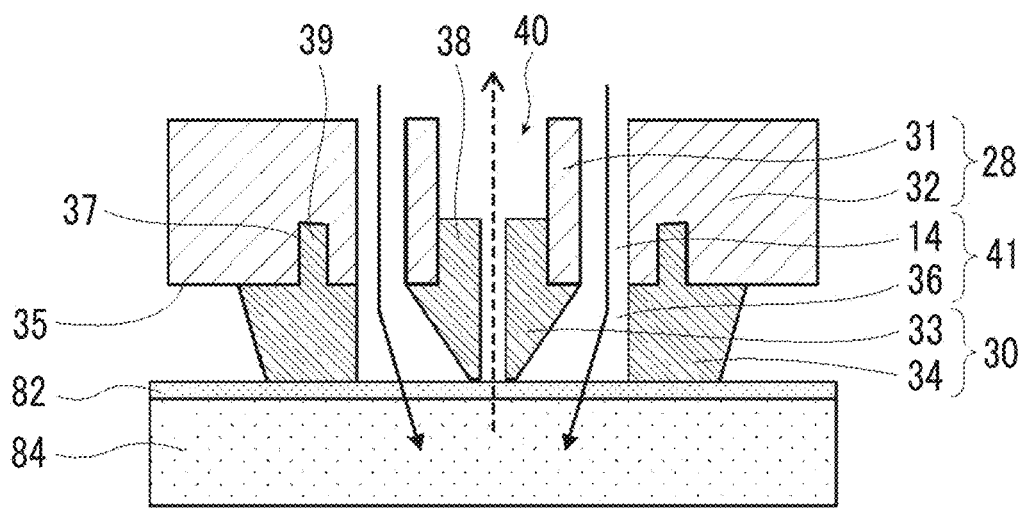
FIG. 10 is a cross-sectional view schematically illustrating the adapter of the imaging apparatus illustrated in FIG. 9.

FIG. 10 is a cross-sectional view schematically illustrating the main body 28 of the imaging apparatus illustrated in FIG. 9 and the adapter 30 bonded to the main body 28.

Figure 11A:
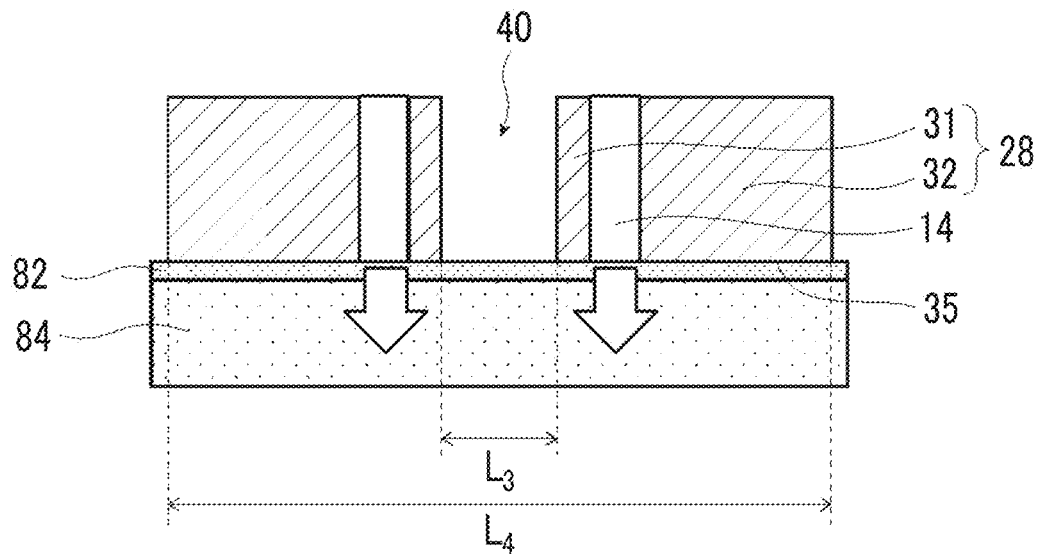
FIG. 11A is a cross-sectional view schematically illustrating a state before the adapter illustrated in FIG. 9 is attached to a main body.
Figure 11B:
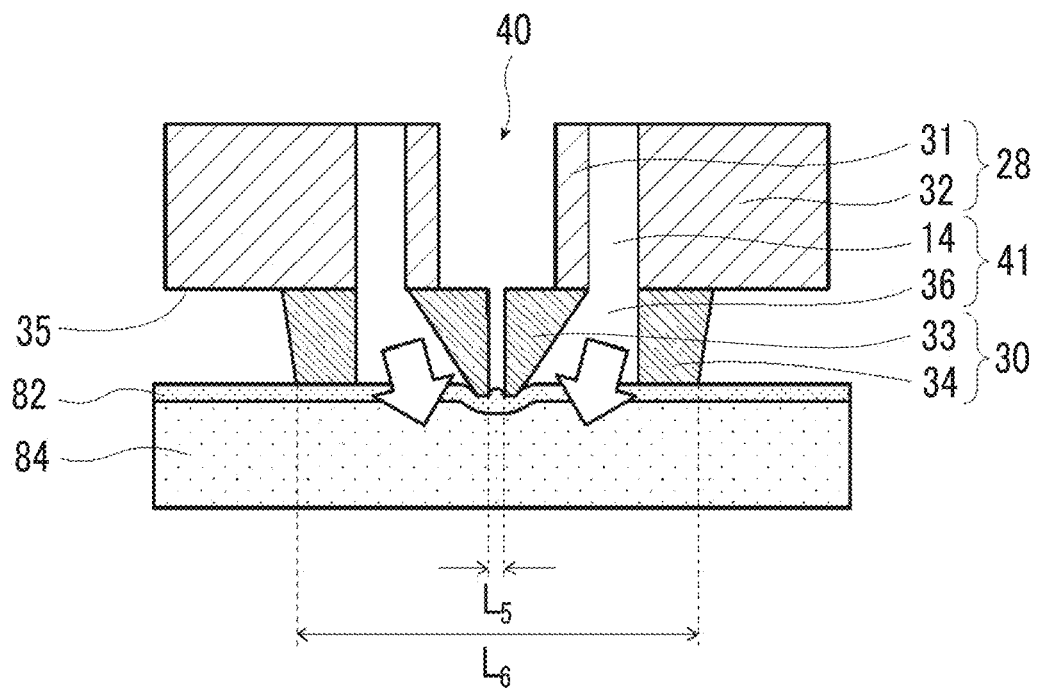
FIG. 11B is a cross-sectional view schematically illustrating a state in which the adapter illustrated in FIG. 9 is attached to the main body and presses the surface of the skin.

FIG. 11A illustrates a state before the adapter 30 is attached to a distal end portion 35 of the main body 28 and FIG. 11B illustrates a state in which the adapter 30 is attached to the distal end portion 35 of the main body 28.

As illustrated in FIG. 10, the main body 28 is configured by integrating a pressing unit main body 31 which is a cylindrical member without the distal end portion (the opening portion on the light receiving side) of the pressing unit 2 according to Embodiment 1 and an illumination unit main body 32 which is a cylindrical member without the distal end portion (the opening portion on the light emission side) of the light shielding member 16 of the illumination unit 4 according to Embodiment 1. A ring-shaped fitting groove 37 for fitting and engaging the adapter 30 is provided in the illumination unit main body 32.

The adapter 30 includes a pressing member 33 that is attached to the pressing unit main body 31 and directly presses the surface of the skin and a light shielding member 34 (second light shielding member) that is attached to the illumination unit main body 32 and is provided on the outer circumferential side of the pressing member 33. Each of the pressing member 33 and the light shielding member 34 is attachable to and detachable from the distal end portion 35 of the main body 28. The pressing member 33 has a ring-shaped convex portion 38 in an upper part which is fitted to an inner cavity surface (inner circumferential surface) of the pressing unit main body 31 of the main body 28 in a case in which the adapter 30 is attached to the main body 28. The light shielding member 34 has a ring-shaped convex portion 39 in an upper part which is fitted to the fitting groove 37 of the illumination unit main body 32.

For the main body 28 and the adapter 30, the adapter 30 can be attached to the distal end portion 35 of the main body 28 by fitting the convex portion 38 of the pressing member 33 to the inner cavity of the pressing unit main body 31 and fitting the convex portion 39 of the light shielding member 34 to the fitting groove 37 of the illumination unit main body 32.

The pressing unit main body 31 and the pressing member 33 which are integrated with each other have a circular central through hole 40 through which the reflected light transmitted through the inside of the skin passes. In addition, a ring-shaped light guide slit 41 that guides illumination light emitted from the illumination unit main body 32 to the surface of the skin is formed between an outer circumferential surface of the pressing unit main body 31 and the pressing member 33 which are integrated with each other and an inner circumferential surface of the illumination unit main body 32 and the light shielding member 34 which are integrated with each other.

The pressing member 33 of the adapter 30 has a conical nozzle shape having a circular through hole therein. Similarly to the pressing unit 2 according to Embodiment 1, in a state in which the distal end portion (the opening portion on the light receiving side) of the pressing member 33 comes into close contact with the surface of the skin such that an observation part (a skin surface captured by the imaging unit 6) is located in a circular tube, the pressing member 33 is pressed against the surface of the skin to curve the surface of the skin which is the observation part. In addition, the pressing member 33 also functions as a light shielding member which shields light such that irradiation light emitted from the illumination unit to the surface of the surface or specularly reflected light from the surface of the surface is not directly incident on the imaging unit.

The light shielding member 34 of the adapter 30 has a cylindrical shape with an inside diameter that is greater than the maximum outside diameter of the pressing member 33 of the adapter 30 and is provided on the outer circumferential side of the pressing member 33. A ring-shaped light guide slit 36 is formed between the outer circumferential surface of the pressing member 33 and the inner circumferential surface of the light shielding member 34. The distal end portion (the opening portion on the light emission side) of the light shielding member 34 is located slightly behind the distal end portion (the opening portion on the light receiving side) of the pressing member 33. In other words, the pressing member 33 protrudes from the light shielding member 34.

The inside diameter of the pressing member 33 of the adapter 30 can be different from the inside diameter of the pressing unit main body 31 of the main body 28. That is, the diameter $L_5$ of the view field ring of the pressing member 33 of the adapter 30 can be set to be different from the diameter $L_3$ of the view field ring of the pressing unit main body 31 of the main body 28.

The outside diameter of the light shielding member 34 of the adapter 30 can be different from the outside diameter of the illumination unit main body 32 of the main body 28. That is, the diameter $L_6$ of the light shielding member 34 of the adapter 30 can be set to be different from the diameter $L_4$ of the illumination unit main body 32 of the main body 28.

The distal end portion (the opening portion on the light receiving side) of the pressing member 33 of the adapter 30 protrudes from the distal end portion (the opening portion on the light emission side) of the light shielding member 34 of the adapter 30. The amount of protrusion (that is, a distance from a close contact surface between the light shielding member 34 and the surface of the skin to a close contact surface between the pressing member 33 and the surface of the skin) can be set according to the amount of deformation of the skin at the time of pressing (the depth of a recess generated in the skin in a case in which the skin is pressed).

Therefore, in a case in which adapters corresponding to an observation target and the thickness of the epidermis in each part of the body are manufactured in advance, it is possible to acquire appropriate images only by switching the adapter according to the observation target or the observation part.

Specifically, as illustrated in FIG. 11B, as an observation part (view field) and a region irradiated with illumination light become closer to each other, diffused transmitted light becomes brighter. Therefore, it is possible to improve the brightness of a captured image.

In addition, in a case in which the diameter of the distal end portion of the light shielding member 34 of the adapter is small, for example, if the imaging apparatus 1 is placed on each part of the face, such as parts around the eyes or the mouth, the pressing unit or the light shielding member can be brought into close contact with the surface of the skin, without being interfered by the unevenness of the surface of the skin or parts such as the eyes and the nose.

In addition, in a case in which adapters having view field diameters or outside diameters corresponding to the thickness of the epidermis in each part of the body are manufactured in advance, it is possible to use the adapter corresponding to the observation part.

In the above-mentioned adapter, the height of the pressing member 33 may be changed. For example, in a case in which there are depressions or wrinkles in the surface of the skin, the height of the pressing member 33 is increased by 0.5 mm to reliably shield irradiation light leaking from the light guide slit 36 or directly reflected light from the surface of the skin.

EXAMPLES

Example 1

A central portion of the cheek of the subject was captured by the imaging apparatus 1 according to Embodiment 1 (using the pressing unit 2 with a projection amount of 1.0 mm) to acquire a Gi image.

Comparative Example 1

A central portion of the cheek of the subject was captured by an imaging apparatus in which the pressing unit 2 of the imaging apparatus 1 according to Embodiment 1 did not protrude from the light shielding member 16 of the illumination unit 4 to obtain a G image.

Figure 12A:
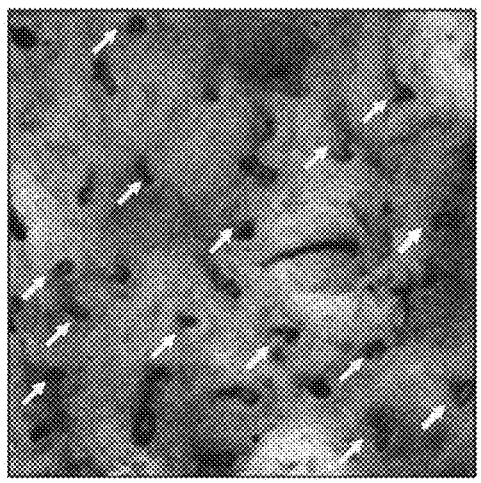
FIG. 12A illustrates a G component image according to Example 1.
Figure 12B:
FIG. 12B illustrates a G component image according to Comparative Example 1.

FIG. 12A illustrates the G image according to Example 1 and FIG. 12B illustrates the G image according to Comparative Example 1.

In FIG. 12A, in the G image according to Example 1 in which the periphery of an observation region is pressed by the pressing unit 2, the capillary in the papillary process indicated by an arrow in FIG. 12A can be confirmed.

In contrast, as illustrated in FIG. 12B, in the G image according to Comparative Example 1 in which the periphery of an observation part is not pressed, it is difficult to confirm the capillary in the papillary process.

As such, in a case in which the surface of the skin is pressed by the pressing unit 2, it is possible to appropriately observe the capillary in the papillary process.

Example 2

Similarly to Example 1, a part inside the forearm of the subject was captured by the imaging apparatus 1 according to Embodiment 1 to acquire an RGB image.

Comparative Example 2

A part inside the forearm of the subject was captured by the same imaging apparatus as that according to Comparative Example 1 to acquire an RGB image.

Figure 13A:
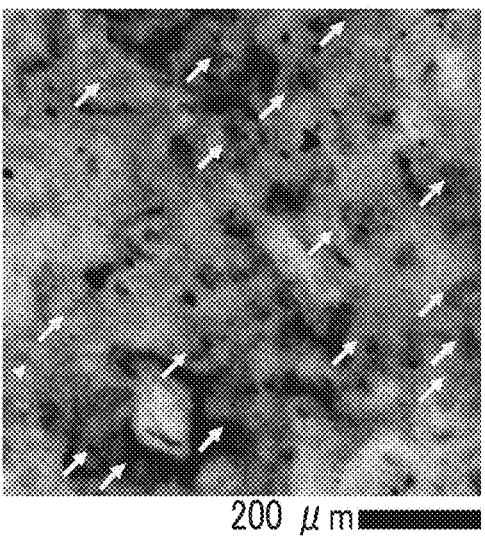
FIG. 13A illustrates an RGB image according to Example 2.
Figure 13B:
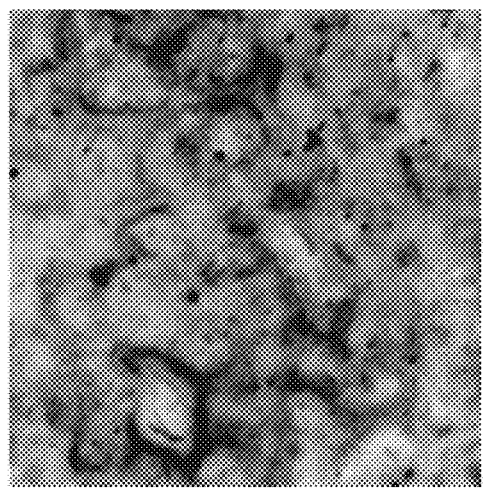
FIG. 13B illustrates an RGB image according to Comparative Example 2.

FIG. 13A illustrates the RGB image according to Example 2 and FIG. 13B illustrates the RGB image according to Comparative Example 2. In FIGS. 13A and 13B, a brown portion indicates melanin and a looped red portion indicates the capillary in the papillary process.

Similarly to Example 1, in the RGB image according to Example 2 in which the periphery of the observation region is pressed by the pressing unit 2, the capillary in the papillary process indicated by an arrow in FIG. 13A can be confirmed.

In contrast, in the RGB image according to Comparative Example 2 in which the periphery of the observation region is not pressed, it is difficult to confirm the capillary in the papillary process.

These results prove that, in a case in which the periphery of the observation region is pressed by the pressing unit 2, it is possible to appropriately observe the capillary in the papillary process.

In addition, since the RGB image was acquired, it was possible to clearly distinguish and observe a melanin pigment (brown portion) and the capillary (looped red portion) in the papillary process from a difference in color.

Reference Example 1

A skin evaluation method using the image acquired by the imaging apparatus 1 according to Embodiment 1 is provided.

FIG. 6A illustrates an RGB image acquired by capturing the cheek of a certain subject using the imaging apparatus 1 and FIG. 6B illustrates an RGB image acquired by capturing a part around the eye.

A portion surrounded by a dotted line in FIGS. 6A and 6B corresponds to the papillary structure. The comparison between FIG. 6A and FIG. 6B showed that the number density of the capillaries in the papillary processes (capillary number density) in the cheek was higher than that in the part around the eye.

EXPLANATION OF REFERENCES

1: imaging apparatus
2: pressing unit (first light shielding member)
4, 4A, 4B, 4C: illumination unit
6: imaging unit
8: image processing apparatus (PC)
10: display device
12, 12A, 12B: light source
14, 41: light guide slit
16: light shielding member (second light shielding member)
18: objective lens
20: driving unit
22: camera
24: optical fiber cable
26: resin
28: main body
30: adapter
31: pressing unit main body
32: illumination unit main body
33: pressing member
34: light shielding member
35: distal end portion of main body
36: light guide slit of adapter
37: fitting groove
38, 39: convex portion
40: central through hole
80: horny layer
82: epidermis
84: dermis
86: base layer
87: epidermal process
88: papillary layer
89: papillary process
90: reticular layer
92: blood vessel (reticular layer blood vessel) in reticular layer
94: capillary (loop) in papillary process
96: melanin pigment
97: concave portion of papillary layer
R, $R_1$, $R_2$: illumination radius
$D_1$, $D_2$: maximum depth
S: skin tissue (skin)
$L_1$: amount of protrusion
$L_2$: width of light guide slit
$L_3$: diameter of inner hole (view field ring) of pressing member of main body
$L_4$: diameter of light shielding member of main body
$L_5$: diameter of inner hole (view field ring) of pressing member of adapter
$L_6$: diameter of light shielding member of adapter

What is claimed is:

1. An imaging apparatus for acquiring an image of a papillary structure or a capillary in a papillary layer, the imaging apparatus comprising:
   an illumination unit that irradiates a surface of a skin with illumination light;
   an imaging unit that captures transmitted light reflected from the inside of the skin;
   a light shielding unit that is brought into close contact with the surface of the skin, is used, and is provided so as to prevent light reflected from the surface of the skin from reaching the imaging unit; and
   a pressing unit having a distal end that presses the surface of the skin in order to curve an epidermis of the skin through which the transmitted light to be captured passes.

2. The imaging apparatus according to claim 1, wherein the light shielding unit has a tubular shape and is opened in a normal direction to a sensor surface of the imaging unit.

3. The imaging apparatus according to claim 2, wherein the light shielding unit has a cylindrical shape.

4. The imaging apparatus according to claim 1, wherein the illumination unit emits the illumination light such that the surface of the skin is illuminated in a ring shape.

5. The imaging apparatus according to claim 1, wherein the pressing unit is provided at a distal end of the light shielding unit and is formed as a first light shielding member that is integrated with the light shielding unit.

6. The imaging apparatus according to claim 5, wherein the pressing unit has a tubular shape with the same inside diameter as that of the light shielding unit and is opened in the normal direction to the sensor surface of the imaging unit.

7. The imaging apparatus according to claim 1, wherein the pressing unit has a pressing unit main body and a pressing member that is attached to the pressing unit main body and directly presses the surface of the skin,
   the illumination unit has an illumination unit main body from which the illumination light is emitted and a second light shielding member that is attached to the illumination unit main body and is provided on an outer circumferential side of the pressing member,
   the pressing unit main body and the illumination unit main body are integrated to form a main body of the imaging apparatus,
   the pressing member and the second light shielding member form an adapter that is attached to a distal end portion of the main body,
   the pressing member has a conic nozzle shape having a circular through hole therein,
   the second light shielding member has a cylindrical shape with an inside diameter greater than a maximum outside diameter of the pressing member, and
   the pressing member and the second light shielding member form a ring-shaped light guide slit that guides the illumination light emitted from the illumination unit main body to the surface of the skin between an outer circumferential surface of the pressing member and an inner circumferential surface of the light shielding member.

8. The imaging apparatus according to claim 1,
wherein the distal end of the pressing unit protrudes from a distal end of the illumination unit, and
a distance between a close contact surface between the illumination unit and the surface of the skin and a close contact surface between the pressing unit and the surface of the skin in the normal direction to the sensor surface of the imaging unit is in a range of 0.1 mm to 1.0 mm.

9. The imaging apparatus according to claim 1,
wherein a distance between an optical axis of the illumination light emitted from the illumination unit and an optical axis of the transmitted light received by the imaging unit in a horizontal direction of the sensor surface of the imaging unit is in a range of 0.5 mm to 50 mm.

10. The imaging apparatus according to claim 1,
wherein the illumination unit includes a plurality of light sources, and
the plurality of light sources are symmetrically arranged.

11. The imaging apparatus according to claim 10,
wherein the light source is an LED, an incandescent lamp, a fluorescent lamp, or a discharge lamp.

12. The imaging apparatus according to claim 10,
wherein the illumination unit further includes a cylindrical second light shielding member with an inside diameter larger than an outside diameter of the pressing unit,
the second light shielding member is provided on an outer circumferential side of the pressing unit,
a ring-shaped light guide slit is formed between an outer circumferential surface of the pressing unit and an inner circumferential surface of the second light shielding member, and
the illumination light is emitted from the light sources to the surface of the skin through the light guide slit.

13. The imaging apparatus according to claim 10,
wherein the illumination unit further includes an optical fiber cable, and
the illumination light is emitted from the light sources to the surface of the skin through the optical fiber cable.

14. The imaging apparatus according to claim 1,
wherein the illumination unit comprises a transparent cover member provided in a portion that comes into contact with the surface of the skin.

15. The imaging apparatus according to claim 1,
wherein the imaging unit includes an objective lens.

16. An image display system comprising:
the imaging apparatus according to claim 1; and
a display device that displays an image acquired by the imaging unit.

17. The image display system according to claim 16,
further comprising:
an image processing apparatus that performs image processing on the basis of the image acquired by the imaging unit of the imaging apparatus,
wherein the display device displays an image processed by the image processing apparatus.

18. The image display system according to claim 16,
wherein the display device displays an RGB image, and
the RGB image includes an image corresponding to a papillary structure and a capillary in a papillary process.

19. The image display system according to claim 18,
wherein the RGB image further includes an image corresponding to a reticular layer blood vessel.

20. The image display system according to claim 16,
wherein the RGB image includes a looped brown portion and a looped red portion surrounded by the looped brown portion.

21. The image display system according to claim 20,
wherein the looped brown portion is a melanin pigment included inside the skin, and
the looped red portion surrounded by the looped brown portion is the capillary in the papillary process.

22. An image display method for displaying an image of a papillary structure or a capillary in a papillary layer using the image display system according to claim 16, the method comprising:
a first irradiation step of pressing a surface of a skin in order to curve an epidermis of the skin through which transmitted light to be captured passes and irradiating the surface of the skin with illumination light;
a first image signal acquisition step of capturing only transmitted light reflected from the inside of the skin to acquire a first image signal of the skin whose epidermis has been curved;
a first image formation step of forming an image of the skin whose epidermis has been curved on the basis of the first image signal; and
an image display step of displaying the image of the skin whose epidermis has been curved on a monitor.

23. The image display method according to claim 22,
further comprising:
a second irradiation step of irradiating the surface of the skin with irradiation light;
a second image signal acquisition step of capturing only the transmitted light reflected from the inside of the skin to acquire a second image signal of the skin whose epidermis has not been curved in the same region as that including a position where the image of the skin whose epidermis has been curved is captured;
a second image formation step of forming an image of the skin whose epidermis has not been curved on the basis of the second image signal; and
an image display step of displaying the image of the skin whose epidermis has been curved and the image of the skin whose epidermis has not been curved on the monitor.

24. The image display method according to claim 23,
wherein, in the first image formation step, a first RGB image of the skin whose epidermis has been curved is formed on the basis of the first image signal,
in the second image formation step, a second RGB image of the skin whose epidermis has not been curved is formed on the basis of the second image signal,
in the image display step, the first RGB image and the second RGB image are displayed on the monitor at the same time, and
the first and second RGB images include an image corresponding to a papillary structure and a capillary in a papillary process.

25. The image display method according to claim 24,
wherein the first RGB image and the second RGB image include a looped brown portion and a looped red portion surrounded by the looped brown portion,
the looped brown portion is a melanin pigment included inside the skin,
the looped red portion surrounded by the looped brown portion is the capillary in the papillary process, and the second image signal related to the looped red portion acquired in the second image signal acquisition step is weaker than the first image signal related to the looped red portion acquired in the first image signal acquisition step.

26. The image display method according to claim 25, wherein, in the second image formation step, the second RGB image is formed on the basis of the second image signal weaker than the first image signal related to the looped red portion acquired in the first image signal acquisition step.

* * * * *